(12) United States Patent
Kim

(10) Patent No.: US 10,772,920 B2
(45) Date of Patent: Sep. 15, 2020

(54) COMPOSITION CONTAINING EXTRACELLULAR POLYSACCHARIDE PRODUCED BY CERIPORIA LACERATA AS ACTIVE INGREDIENT FOR IMMUNOREGULATION

(71) Applicant: FUGENBIO CO., LTD., Seoul (KR)

(72) Inventor: Yoon Soo Kim, Seongnam-si (KR)

(73) Assignee: FUGENBIO CO., LTD., Seoul (KR)

( * ) Notice: Subject to any disclaimer, the term of this patent is extended or adjusted under 35 U.S.C. 154(b) by 14 days.

(21) Appl. No.: 15/751,516

(22) PCT Filed: Jul. 22, 2016

(86) PCT No.: PCT/KR2016/008030
§ 371 (c)(1),
(2) Date: Feb. 9, 2018

(87) PCT Pub. No.: WO2017/026697
PCT Pub. Date: Feb. 16, 2017

(65) Prior Publication Data
US 2018/0228852 A1 Aug. 16, 2018

(30) Foreign Application Priority Data

Aug. 12, 2015 (KR) .......................... 10-2015-0113998
Oct. 5, 2015 (KR) .......................... 10-2015-0139583
Jun. 13, 2016 (KR) .......................... 10-2016-0072982

(51) Int. Cl.
| | | |
|---|---|---|
| A01N 65/00 | (2009.01) | |
| A61K 36/06 | (2006.01) | |
| A61K 36/09 | (2006.01) | |
| A61K 39/00 | (2006.01) | |
| A61K 39/38 | (2006.01) | |
| A01N 63/00 | (2020.01) | |
| A01N 63/04 | (2006.01) | |
| A61K 36/07 | (2006.01) | |
| A61P 37/04 | (2006.01) | |
| A23L 31/00 | (2016.01) | |
| A23L 33/10 | (2016.01) | |

(52) U.S. Cl.
CPC .............. *A61K 36/07* (2013.01); *A23L 31/00* (2016.08); *A23L 33/10* (2016.08); *A61P 37/04* (2018.01); *A23V 2002/00* (2013.01); *A61K 2236/00* (2013.01)

(58) Field of Classification Search
CPC ...... A61K 36/07; A61K 36/074; A61K 38/00; A61K 39/0002; A01N 63/04
See application file for complete search history.

(56) References Cited

U.S. PATENT DOCUMENTS

| | | | | |
|---|---|---|---|---|
| 10,226,494 B2* | 3/2019 | Kim | ........................ | A61Q 19/00 |
| 2014/0193454 A1* | 7/2014 | Kim | ........................ | A61K 36/07 |
| | | | | 424/195.15 |
| 2014/0193455 A1* | 7/2014 | Kim | ........................ | A61K 36/07 |
| | | | | 424/195.15 |
| 2017/0333501 A1* | 11/2017 | Kim | ........................ | A61Q 19/00 |
| 2017/0360860 A1* | 12/2017 | Kim | ........................ | A61K 36/06 |
| 2019/0008748 A1* | 1/2019 | Kim | ........................ | A61K 8/60 |

FOREIGN PATENT DOCUMENTS

| | | | |
|---|---|---|---|
| JP | 20133209348 | * | 10/2013 |
| KR | 10-2007-0014745 A | | 2/2007 |
| KR | 10-1031605 B1 | | 4/2011 |
| KR | 1020100112236 | * | 4/2011 |
| KR | 10-2014-0019113 A | | 2/2014 |
| KR | 10-2014-0036504 A | | 3/2014 |

OTHER PUBLICATIONS

Heathline, Autoimmune Diseases: Types, Symptoms, Causes and More, https://www.healthline.com/health/autoimmune-disorders, accessed on Jan. 4, 2019. (Year: 2019).*
Francois, Nature Protocols, 2006; 1: 2995-3000 (Year: 2006).*
Korea Intellectual Property Office, Office Action of Korean Patent Application No. 10-2016-0072982 dated Oct. 20, 2016.
International Searching Authority, International Search Report of PCT/KR2016/008030 dated Dec. 2, 2016 [PCT/ISA/210].

* cited by examiner

*Primary Examiner* — Gary B Nickol
*Assistant Examiner* — Lakia J Jackson-Tongue
(74) *Attorney, Agent, or Firm* — Sughrue Mion, PLLC

(57) ABSTRACT

The present invention relates to an extracellular polysaccharide produced by *Ceriporia lacerata*, a culture medium of *Ceriporia lacerata* hyphae including the extracellular polysaccharide, a composition for immunoregulation containing, as an active ingredient, dried powder of the hyphae culture medium or an extract of the hyphae culture medium, a pharmaceutical composition for preventing or treating an immune disease, and a health food for immunoregulation. The composition of the present invention has an excellent effect on immune enhancement and overactive immune response inhibition.

15 Claims, 1 Drawing Sheet
Specification includes a Sequence Listing.

[Fig. 1]
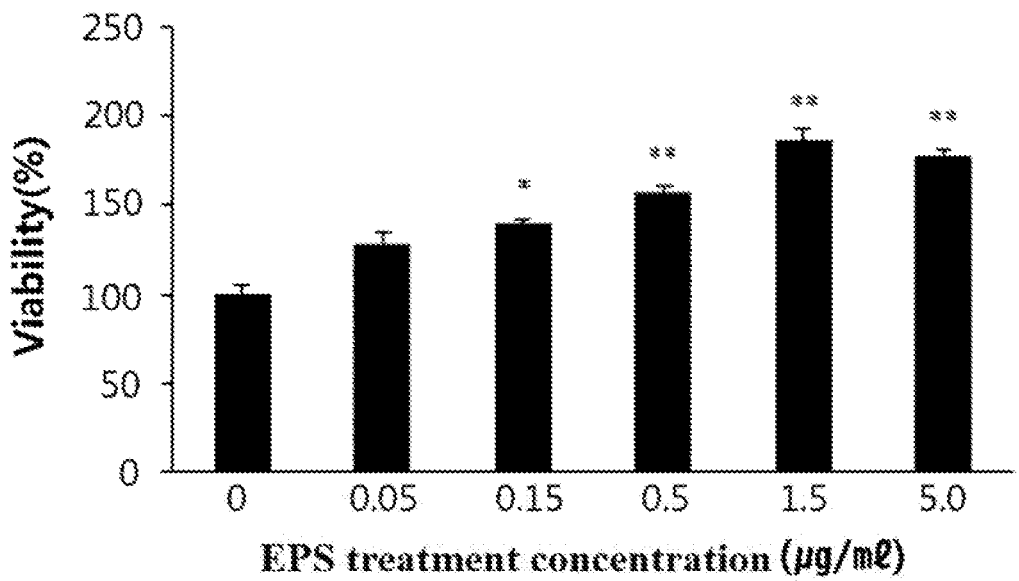
[Fig. 2]
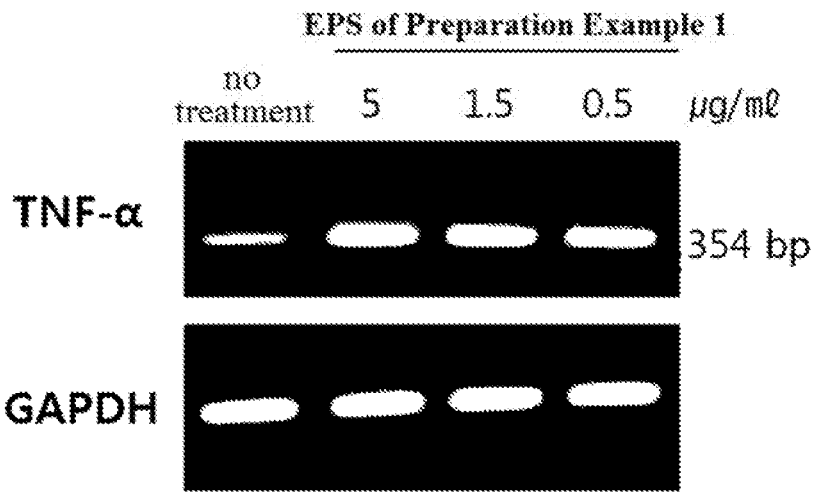
[Fig. 3]
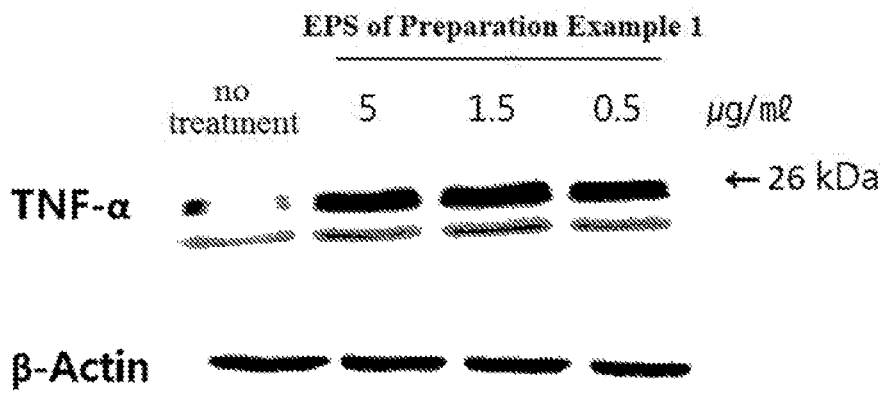

SEQUENCE LISTING

```
<160> NUMBER OF SEQ ID NOS: 4

<210> SEQ ID NO 1
<211> LENGTH: 32
<212> TYPE: RNA
<213> ORGANISM: Artificial Sequence
<220> FEATURE:
<223> OTHER INFORMATION: TNF-alpha forward primer

<400> SEQUENCE: 1
ttctgtctac tgaacttcgg ggtgatcggt cc                              32

<210> SEQ ID NO 2
<211> LENGTH: 32
<212> TYPE: RNA
<213> ORGANISM: Artificial Sequence
<220> FEATURE:
<223> OTHER INFORMATION: TNF-alpha reverse primer

<400> SEQUENCE: 2
gtatgagata gcaaatcggc tgacggtgtg gg                              32
```

```
<210> SEQ ID NO 3
<211> LENGTH: 20
<212> TYPE: RNA
<213> ORGANISM: Artificial Sequence
<220> FEATURE:
<223> OTHER INFORMATION: GAPDH forward primer

<400> SEQUENCE: 3
agatccacaa cggatacatt                                               20

<210> SEQ ID NO 4
<211> LENGTH: 20
<212> TYPE: RNA
<213> ORGANISM: Artificial Sequence
<220> FEATURE:
<223> OTHER INFORMATION: GAPDH reverse primer

<400> SEQUENCE: 4
tccctcaaga ttgtcagcaa                                               20
```

COMPOSITION CONTAINING EXTRACELLULAR POLYSACCHARIDE PRODUCED BY CERIPORIA LACERATA AS ACTIVE INGREDIENT FOR IMMUNOREGULATION

CROSS REFERENCE TO RELATED APPLICATIONS

This application is a National Stage of International Application No. PCT/KR2016/008030, filed Jul. 22, 2016, claiming priorities based on Korean Patent Application Nos. 10-2015-0113998, filed Aug. 12, 2015, 10-2015-0139583, filed Oct. 5, 2015 and 10-2016-0072982, filed Jun. 13, 2016, the contents of all of which are incorporated herein by reference in their entirety.

TECHNICAL FIELD

The present invention relates to a composition for immune modulation comprising an extracellular polysaccharide produced by *Ceriporia lacerata*, a mycelial culture medium of *Ceriporia lacerata* containing the same, dried powders of the mycelial culture medium, or an extract of the mycelial culture medium, as an effective ingredient.

BACKGROUND ART

The immune system can be divided into natural resistance, non-specific immune system and specific immune system. Natural resistance (primary defense line) refers to the anatomical and physiological components that block all intruders such as microbes regardless of their type. Further, Non-specific immune system (secondary defense line) refers to a defense system consisting of phagocytes that eliminate intruders which have broken the natural resistance and entered into a body. Also, specific immune system (tertiary defense line) refers to an immune system consisting of lymphocytes. Among them, specific immune system is a highly developed immune system having memory capacity and the ability to distinguish between self and non-self (Richard A. Goldsby, et al., *KUBY Immunology*, 2000).

Leukocytes constitute a secondary or tertiary defense line and take charge of foreign bodies that have broken the primary defense line. In the case of bacterial or viral infection or inflammatory reaction, the regulation of activities of macrophages and lymphocytes plays a crucial role in determining the therapeutic effect of a medicine. The macrophage is a main cell involved in the immune response, and known to serve various functions such as secreting cytokines to regulate the action of immune cells, destroying microbes, antigens, and dead tissues by phagocytosis in natural immunity, acting as an effector cell in humoral immune responses, eliminating antigens in delayed type hypersensitivity, destroying tumor cells by secreting Tumor Necrosis Factor-α (TNF-α), antigen processing and presentation in acquired immune responses, regulating immune responses by secreting inflammation-related substances or cytokines, healing damaged tissues by producing growth factors for fibroblast and vascular endothelial, etc. In addition, the macrophage plays a protective role against disorders such as infection and cancer, and secretes inflammatory cytokines and chemical mediators by inflammatory stimuli. Lipopolysaccharide, a membrane constituent of Gram-negative bacteria, is known to activate macrophages to secrete TNF-α, interleukin-1 (IL-1), IL-6, IL-10, prostanoids and nitric oxide.

Studies have been actively conducted to treat various disorders by enhancing immunity through regulating intracellular levels of the above-mentioned factors related to immunity, and initially, chemical substances were used to regulate intracellular levels of the factors, but they had a disadvantage of severe side effects, and recently, studies have been actively conducted to regulate intracellular levels of the above factors using nature derived substances which show no or very low side effects.

With regard to the above, Korean Patent Publication No. 2014-0019113 discloses a therapeutic or prophylactic activity of an α-galactosylceramide analogue on disorders due to abnormal immune modulation, and Korean Patent No. 10-1417341 discloses a composition for preventing and treating inflammatory or immune disorders comprising *Sargassum muticum* extract and an apo-9'-fucoxanthinone compound.

Meanwhile, it is known that *Ceriporia lacerata* is a kind of white-rotting fungus and conducts co-metabolism, i.e., lignin decomposition, in order to use carbon sources such as cellulose, hemi-cellulose, other polysaccharides, and glycerol, etc., in the ecosystem.

Regarding the use of *Ceriporia lacerata* in medical treatment, only the use of the extract of the culture medium of *Ceriporia lacerata* disclosed in Korean Patent No. 10-1031605 in the treatment of in diabetes is known so far. However, it has not been reported that *Ceriporia lacerata* has immune modulating effect yet.

Accordingly, the present inventors have found that an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium shows immune modulating effect, and have completed the present invention.

DISCLOSURE OF INVENTION

Technical Problem

It is an object of the present invention to provide a composition for immune modulation, a pharmaceutical composition for the prevention or treatment of an immune disorder and a health functional food for immune modulation, which contain an active ingredient produced by *Ceriporia lacerata*.

It is another object of the present invention to provide a method for immune modulation comprising administering an active ingredient produced by *Ceriporia lacerata*, and a use of the active ingredient for preparing a drug for immune modulation.

Solution to Problem

In accordance with one object of the present invention, there is provided a composition for immune modulation, a pharmaceutical composition for the prevention or treatment of an immune disorder, and a health functional food for immune modulation, which contain an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a method for immune modulation comprising administering an active ingredient produced by Ceriporia lacerata, and a use of the active ingredient for preparing a drug for immune modulation Advantageous Effects of Invention A composition for immune modulation, a pharmaceutical composition for the prevention or treatment of an immune disorder, and a health functional food for immune modulation of the present invention inhibit excessive lymphocyte proliferation, and thus show an excellent effect of inhibition of excessive immunity. In addition, the composition and the health functional food of the present invention show an excellent immune enhancing activity such as increasing splenocyte proliferation capability and increasing TNF-α expression to activate macrophages, etc.

BRIEF DESCRIPTION OF DRAWINGS

FIG. 1 is a graph showing the lymphocyte proliferation capability (%) after treating mouse-derived splenocytes with the extracellular polysaccharide (EPS) produced by Ceriporia lacerata at various concentrations (** $p<0.01$, * $p<0.05$).

FIG. 2 shows the results of agarose gel electrophoresis verifying the expression of TNF-α mRNA after treating mouse-derived peritoneal macrophages with an extracellular polysaccharide produced by Ceriporia lacerata at various concentrations.

FIG. 3 is a Western blot result verifying the expression of TNF-α protein after treating mouse-derived peritoneal macrophages with an extracellular polysaccharide produced by Ceriporia lacerata at various concentrations.

BEST MODE FOR CARRYING OUT THE INVENTION

In the present invention, there is provided a composition for immune modulation, which contains an extracellular polysaccharide produced by Ceriporia lacerata; a mycelial culture medium of Ceriporia lacerata containing the extracellular polysaccharide; dried powders of the mycelial culture medium; or an extract of the mycelial culture medium, as an effective ingredient.

As used herein, the term "extracellular polysaccharide (EPS)" refers to a part of the cell wall of a microorganism such as fungi, which means a polysaccharide secreted extracellularly to form a capsule therearound, or a substance secreted as mucilage around cells or into media. The extracellular polysaccharide is secreted by microorganisms to protect themselves from the external environment such as antibodies, toxic substances, protozoa, and bacteriophages, etc.

In the above composition, the extracellular polysaccharide may comprise 40 to 60 wt % of sugar and 30 to 40 wt % of protein, 40 to 50 wt % of sugar and 32 to 38 wt % of protein, or 43 to 47 wt % of sugar and 33 to 36 wt % of protein, specifically about 45 wt % of sugar and about 34 wt % of protein.

The sugar may include mannose, galactose and glucose.

The extracellular polysaccharide may have a molecular weight of 100 to 150 kDa, 110 to 140 kDa or 115 to 125 kDa, more specifically about 120 kDa.

According to one embodiment of the present invention, the extracellular polysaccharide may be prepared by a preparation method comprising the steps of: (a) culturing mycelia of Ceriporia lacerata in a liquid to prepare a mycelial culture medium of Ceriporia lacerata, (b) drying the mycelial culture medium of Ceriporia lacerata to form powders, and (c) extracting the powders of the mycelial culture medium of Ceriporia lacerata with a solvent, and filtering and concentrating the resultant extract under reduced pressure.

The medium for culturing in a liquid in the step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

Specifically, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.05 to 0.1 wt % of magnesium sulfate ($MgSO_4$), 0.05 to 0.25 wt % of monopotassium phosphate ($KH_2PO_4$), 0.05 to 0.25 wt % of dipotassium phosphate ($K_2HPO_4$) and residual quantity of water.

The culture in a liquid of the step (a) may be conducted under a blue LED light source, and may be conducted with a carbon dioxide concentration maintained at 1,000 to 2,000 ppm.

The culture in a liquid, for example, may be conducted for 8 to 13 days at 20 to 25° C., under a blue LED light source, with the pH maintained at 4.5 to 6.0, an illuminance maintained at 0.1 to 0.8 LUX, an air injected at 0.5 to 2.0 $kgf/cm^2$, a carbon dioxide concentration maintained at 1,000 to 2,000 ppm. Specifically, the culture may be conducted under the condition of 20 to 25° C., pH 4.5 to 6.0, 0.5 to 2.0 $kgf/cm^2$, and carbon dioxide concentration of 1,000 to 2,000 ppm for 5 to 15 days. Culturing in a liquid under the above condition is preferable since it leads a high content of an extracellular polysaccharide produced.

The parent strain for use in step (a) may be a strain by culturing a dominant strain stored in PDA (Potato dextrose agar) medium at 1 to 5° C., in PDB (Potato dextrose broth) medium in Erlenmeyer flask using a shaking incubator at a constant temperature of about 25° C. for 7 to 9 days. In addition, the culture medium or obtained mycelium can be used as an inoculum after the parent strain is cultured as described above. Specifically, the amount of the mycelium to be inoculated may be about 0.5% (w/v) based on the solution to be cultured. Since a high amount of the mycelia (%/100 mL, w/v) does not necessarily result in a high content of the extracellular polysaccharide, the medium composition may be preferably selected such that it provides a condition for maximizing the content of extracellular polysaccharide, rather than the best nutritional ratio and environmental condition for the growth of mycelia.

The culture medium may be separated and purified into mycelia and an aqueous solution. For the separation and purification, the mycelia may be eliminated from the culture medium using a centrifuge and the remaining solution may be repeatedly purified using a Multi-Sheet Filter Press and a vibrating membrane separator (PALLSEP), followed by irradiation with UV rays for 1 minute. Also, the culture medium may be sealed and stored after removing oxygen, where the presence of mycelia in the medium may result in the change in the content of the effective ingredient due to the growth of the mycelia.

In the step (b), the mycelial culture medium prepared in the step (a) may be dried to form powders. In order to prevent the loss of an effective substance, the drying may be carried out at a temperature of 40° C. or lower, more specifically 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In the step (c), after the dried powders of a mycelial culture medium obtained in the step (b) are extracted with a solvent, an extracellular polysaccharide, an effective ingredient according to the present invention, is isolated.

Specifically, 100 ml of distilled water was added to 3 to 10 g of the dried powders of the mycelial culture medium and suspended well, followed by centrifugation at 5,000 to 10,000 rpm for 10 to 30 minutes to obtain a supernatant. And, then, a 2- to 3-fold amount of extraction solvent may be added to the supernatant, which may then be placed in a refrigerator at 1 to 5° C. and allowed to stand for 10 to 15 hours. The supernatant in the solution which had been allowed to stand may be obtained and centrifuged again at 5,000 to 10,000 rpm for 10 to 30 minutes, and the precipitate may be recovered, thereby preparing a crude extracellular polysaccharide. The crude extracellular polysaccharide may be vacuum freeze-dried at 30° C. or lower to obtain an extracellular polysaccharide.

The extraction solvent may be a solvent selected from the group consisting of water, a lower alcohol having 1 to 4 carbon atoms, acetone, ether, chloroform and ethyl acetate or a mixture thereof, and more specifically, it may be a solvent selected from the group consisting of water, methanol, ethanol, butanol, acetone, and ethyl acetate or a mixture thereof, even more specifically, water or 50 to 80% (v/v) aqueous solution of ethanol The composition for immune modulation may comprise an extracellular polysaccharide in an amount of 0.1 to 80 wt %, specifically 0.1 to 50 wt %, based on the total weight of the composition, and a mycelial culture medium of *Ceriporia lacerata*, dried powders thereof or an extract of the mycelial culture medium may be adequately comprised in an amount which corresponds to the above amount of the extracellular polysaccharide. However, the effective content of an extracellular polysaccharide, a mycelial culture medium containing the extracellular polysaccharide, dried powder, or an extract of the mycelial culture medium may be adequately adjusted according to the method of use and purpose of the composition.

In addition, the composition for immune modulation may be used as a pharmaceutical composition, a health functional food, or the like for the purpose of modulating immune activity and preventing, improving or treating an immune disorder. The amount to be used and the mode of use may be appropriately adjusted according to the purpose.

The composition for immune modulation may show the effect of immune enhancement or inhibition of excessive immunity. The effect of immune enhancement is an effect of immune enhancement by increasing the expression of TNF-α in macrophages or enhancing splenocyte's proliferation capability. The effect of inhibition of excessive immunity is an effect of inhibiting excessive immunity by inhibiting the overexpression of lymphocytes due to a non-specific stimulant in splenocytes. According to one embodiment of the present invention, the composition for immune modulation of the present invention showed the excellent immune enhancing activities such as increasing the expression of TNF-α in macrophages of the administration group and improving splenocyte's proliferation capability in an EPS concentration-dependent manner. In addition, it showed the effect of inhibition of excessive immunity such as inhibiting lymphocyte overexpression due to PMA, a non-specific stimulant, in splenocytes in the administration group in an EPS concentration-dependent manner.

The present invention provides a pharmaceutical composition for preventing or treating an immune disorder comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

The pharmaceutical composition of the present invention shows the effect of prevention or treatment of various immune disorders through the above-mentioned effect of immune enhancement or inhibition of excessive immunity of the active ingredient.

The immune disorder may be at least one selected from the group consisting of dermatitis, allergies, rhinitis, gout, ankylosing spondylitis, rheumatic fever, lupus, fibromyalgia, peritendinitis, type 1 diabetes, scleroderma, degenerative neurological disorder, type 2 diabetes, silicosis, atherosclerosis, vitiligo, conjunctivitis, and autoimmune disorders.

The autoimmune disorder may be at least one selected from the group consisting of rheumatoid arthritis, systemic scleroderma, atopic dermatitis, psoriasis, asthma, Guilian-Barre syndrome, dermatomyositis, polymyositis, multiple sclerosis, autoimmune encephalomyelitis, polyarteritis *nodosa*, temporal arteritis, juvenile diabetes, alopecia areata, pemphigus, aphthous stomatitis, Crohn's disease and Behcet's disease.

It is already known that increased expression of TNF-α in macrophages as described above is effective for the treatment or prevention of rheumatoid arthritis and Crohn's disease (Related documents: see Kim R B, and so on. *J. Rheumatic disorders* 2013; 20 (3): 177-180, and Braun J, Baraliakos X. *Curr. Opin. Rheumatol.* 2009; 21: 324-34). In addition, it is known that the enhancement of the proliferation capability of splenocytes is effective for the treatment and prevention of lupus and atopy (Related documents: see Chae B S, *Nat. Prod. Sci.*, 17: 354, and Kim KBWR, and so on. *Korean Soc. Food Sci., Nutr,* 2015; 44 (8): 1121-1127). Furthermore, it has been found that inhibition of lymphocyte overexpression among splenocytes is effective for the treatment or prevention of rheumatoid arthritis, systemic scleroderma, atopic dermatitis, diabetes, alopecia areata, psoriasis, pemphigus, aphthous stomatitis, polymyositis, multiple sclerosis or autoimmune encephalomyelitis (Related document: see Korean Patent No. 10-1227819).

The above pharmaceutical composition may further comprise suitable carriers, excipients and diluents conventionally used in pharmaceutical compositions, in addition to an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient The pharmaceutical composition according to the present invention may be formulated in various forms for use according to a conventional method. Suitable formulations include, but are not limited to, tablets, pills, powders, granules, sugarcoated pills, hard or soft capsules, solutions, suspensions or emulsions, injections, suppositories, and the like.

The pharmaceutical composition according to the present invention can be prepared into a suitable formulation using a pharmaceutically inert organic or inorganic carrier. That is, in case that the formulation is a tablet, a coated tablet, a sugar-coated tablet or a hard capsule, lactose, sucrose, starch or a derivative thereof, talc, calcium carbonate, gelatin, or stearic acid or a salt thereof may be used. Also, in case that the formulation is a soft capsule, vegetable oil, wax, fat, or semi-solid or liquid polyol may be used. Furthermore, in case that the formulation is in the form of a solution or syrup, water, polyol, glycerol, vegetable oil, and the like may be used.

A composition according to the present invention may further comprise a preservative, a stabilizer, a humectant, an emulsifier, a solubilizer, a sweetener, a coloring agent, an osmotic pressure regulator, an antioxidant, and the like in addition to the above carrier.

A method of administering a composition according to the present invention can be easily selected in accordance with the formulation, which may be oral or parenteral administration. The dosage may vary depending on the patient's age, sex, weight, disease severity, and route of administration, but is generally 5 to 1,000 mg/kg, specifically 10 to 600 mg/kg based on the extracellular polysaccharide, an effective ingredient, which may be administered in one to three divided doses a day. However, such dosage does not limit the scope of the present invention in any way.

A composition according to the present invention not only provides an excellent effect of immune enhancement or inhibition of excessive immunity, but also shows little toxicity and adverse events, and thus can safely be used for the purpose of prevention or treatment of an immune disorder by long-term administration.

In addition, the present invention provides a health functional food for immune modulation, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

The health functional food for immune modulation has an activity of maintaining homeostasis of immune functions by enhancing immune activity or inhibiting or improving excessive immunity.

A health functional food according to the present invention may be in the form of powders, granules, a tablet, a capsule or a drink, and may be a candy, a chocolate, a drink, a gum, a tea, a vitamin complex, or a health supplementary food.

Herein, the content of an extracellular polysaccharide, a mycelial culture medium containing the same, dried powders of the mycelial culture medium, or an extract of the mycelial culture medium according to the present invention comprised in the health functional food may be generally in the range of 0.01 to 50 wt %, specifically 0.1 to 20 wt % based on the weight of the entire food. Also, it may be comprised in the amount of 0.02 to 10 g, specifically 0.3 to 1 g based on 100 mL of a health functional drink.

The food may further comprise a sitologically acceptable food supplementary additive along with an extracellular polysaccharide, a mycelial culture medium of *Ceriporia lacerata* containing the same, dried powders of the mycelial culture medium, or an extract of the mycelial culture medium of the present invention.

The present invention provides a method for immune modulation comprising administering an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium to a subject in need of immune enhancement or inhibition of excessive immunity.

The above subject may be a mammal, more specifically a human.

In addition, the method for immune modulation may be used for the treatment or prevention of disorders requiring immune enhancement or inhibition of excessive immunity, for example, dermatitis, allergies, rhinitis, gout, ankylosing spondylitis, rheumatic fever, lupus, fibromyalgia, peritendinitis, type 1 diabetes, scleroderma, degenerative neurological disorder, type 2 diabetes, silicosis, atherosclerosis, vitiligo, conjunctivitis, and autoimmune disorders.

Also, the present invention provides a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, for preparing a drug for immune modulation.

Such extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium is as described above.

MODE FOR THE INVENTION

Hereinafter, the present invention is explained in detail by Examples. The following Examples are intended to further illustrate the present invention without limiting its scope.

EXAMPLES

Preparation Example 1. Preparation of Culture Medium of *Ceriporia lacerata*, Dried Powders Thereof, Extract, and Extracellular Polysaccharide (Exopolysaccharide; Hereinafter, Referred to as "EPS")

1-1: Preparation of Culture Medium of *Ceriporia lacerata*

*Ceriporia lacerata* isolated from *Quercus serrata* collected at Sangju city, Gyeongbuk province were subcultured to obtain a parent strain, which was subsequently freeze-stored at −80° C., and the freeze-stored strain was cultured with 2 to 3 passages in PDA (Potato dextrose agar) medium (87 plastic bulbs, Difco, Becton Dickinson and Company), and the strain (hereinafter referred to as "PDA culture strain") was stored in a refrigerator at 4° C. until use. Then, 600 mL of the PDB (Potato dextrose broth) medium (Difco, Becton Dickinson and Company) was placed in an Erlenmeyer flask, and then a PDA culture strain was added thereto and shake-cultured at 25° C. for 8 days to obtain a PDB culture strain.

Meanwhile, for the culture of the strain, a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate ($KH_2PO_4$), 0.05 wt % of dipotassium phosphate ($K_2HPO_4$) and residual quantity of water was sterilized for 20 minutes in a 800 L fermenter with the air injected at 1.5 kgf/cm$^2$ at 121° C. Then, the medium was cooled to 23° C., and inoculated with 600 mL of the PDB culture strain as a starter, and *Ceriporia lacerata* mycelia were liquid-cultured in the medium for 10 days at a constant temperature of 23° C., under a blue LED light source, with the air injected at 0.5 to 1.5 kgf/cm$^2$, an illuminance of 0.5 LUX, and a carbon dioxide concentration of 2,000 ppm, to prepare the mycelial culture medium of *Ceriporia lacerata*.

1-2: Preparation of Dried Powders of Culture Medium of *Ceriporia lacerata*

The mycelial culture medium of *Ceriporia lacerata* prepared in the Preparation Example 1-1 was freeze-dried by using a vacuum freeze dryer at 25° C. for 72 hours to form powders, to prepare dried powders of a mycelial culture medium of *Ceriporia lacerata*.

1-3: Preparation of Extract of Culture Medium of *Ceriporia lacerata*

5 g of dried powders of the mycelial culture medium of *Ceriporia lacerata* prepared in Preparation Example 1-2 was added to 100 mL of distilled water and sufficiently suspended, and then the resulting solution was centrifuged at 8,000 rpm for 20 minutes. And then the supernatant separated therefrom was mixed with a 2- to 3-fold amount of ethanol, and allowed to stand for 12 hours at 4° C. Thereafter, the resultant supernatant was taken and an extract of the mycelial culture medium of *Ceriporia lacerata* was prepared therefrom.

1-4: Preparation of EPS from Culture Medium of *Ceriporia lacerata*

The extract of the mycelial culture medium of *Ceriporia lacerata* prepared in Preparation Example 1-3 was further centrifuged at 8,000 rpm for 20 minutes, and then the precipitate was recovered to obtain crude EPS. The crude EPS was vacuum freeze-dried by using a vacuum freeze dryer at 25° C. for 72 hours to obtain an EPS produced by *Ceriporia lacerata*.

Example 1. Evaluation of EPS Properties 1-1: Molecular Weight Measurement of EPS Using Gel Permeation Chromatography (GPC)

The EPS prepared in Preparation Example 1 was dissolved in a solution of 0.1 M $Na_2SO_4$/0.05 M $NaN_3$ (adjusted to pH 4 with glacial acetic acid) to a concentration of 1% (w/v), and then the mixture was centrifuged at 4,000 rpm for 0.5 hour, then the supernatant alone was isolated and filtered with a 0.45 μm syringe filter and analyzed by GPC.

The refractive index of the detector was used for the GPC analysis, and OHpak SB 805 HQ (Shodex, Japan) was used for the GPC column, and 0.1 M $Na_2SO_4$/0.05 M $NaN_3$ (adjusted to pH 4 with glacial acetic acid) was used for the mobile phase, which was allowed to flow at a flow rate of 1.0 mL/min. Standard curves were generated using dextrans (American Polymer Corporation, USA) of different molecular weights (130 kDa, 400 kDa, 770 kDa or 1200 kDa), and the molecular weight of EPS was measured using refractive index (RI) measuring instrument Knauer K-2310 (Germany). The measurement conditions are summarized in Table 1 below.

TABLE 1

|  | Measurement of molecular weight |
|---|---|
| HPLC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 1.0 mL/min |
| Measuring instrument | RI (Knauer K-2310) |

As a result, the molecular weight of EPS of the present invention was about 120 kDa.

1-2: Measurement of Sugar and Protein Contents of EPS

The EPS prepared in Preparation Example 1 was subjected to secondary purification and treated with a protein-hydrolysis enzyme to measure sugar and protein contents.

Specifically, the primary-purified EPS (EPS prepared in Preparation Example 1) was dissolved in distilled water and centrifuged at 8,000 rpm for 20 minutes to separate the supernatant, and then a 2- to 3-fold amount of ethanol was added thereto. The mixture was placed in a refrigerator at 4° C. and allowed to stand for 12 hours. Thereafter, the resultant supernatant alone was centrifuged again at 8,000 rpm for 20 minutes, and the precipitate was recovered to obtain a secondary-purified EPS. And the secondary-purified EPS was dissolved in distilled water and treated with alcalase, a protein-hydrolysis enzyme, at a concentration of 0.5% (w/v) at 50° C. for 30 minutes.

The sugar content was measured by the phenol-sulfuric acid method. Specifically, 25 μL of 80% (w/v) phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

Also, the protein content was measured by BCA method (see Smith P K et al., *Analytical Biochemistry*, 150 (1): 76-85, 1985) and bovine serum albumin was used as a standard.

The sugar and protein contents measured as described above are shown in Table 2 below. The sugar content was 45 to 51 wt % and the protein content was 33 to 34 wt %.

TABLE 2

|  | Yield (%) | Total sugar content (%) | Total protein content (%) |
|---|---|---|---|
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: alkalase 0.5%, 50° C., 30 minutes.
Each value represents mean ± SE (n ≥ 3).

Also, as a result of analyzing sugar composition of EPS, it was found that the EPS mainly contains mannose, galactose and glucose.

Example 2. Verification of Inhibition Effect on Excessive Lymphocyte Proliferation In order to evaluate the inhibition effect of the EPS of Preparation Example 1 on excessive immunity, mouse-derived splenocytes were treated with phorbol 12-myristate 13-acetate (PMA), a non-specific stimulant, and with EPS of various concentrations, and then the inhibition effect on excessive lymphocyte proliferation was examined.

Specifically, female Balb/C mice, about 8 weeks old and weighing about 25 g, were purchased from Hyochang Science, Korea and used in the experiments. The mice were sacrificed by cervical dislocation method, and spleens were aseptically extracted and shredded on a 100 mesh cell strainer on a RPMI 1640 solution to liberate the cells. The suspension including the liberated cells was carefully placed in a container containing Lymphoprep™ and centrifuged at 15° C. for 15 minutes at 2,000 rpm, to remove precipitated erythrocytes. 200 μl each of the splenocytes ($2\times10^6$ cells/ml) from which erythrocytes were removed were aliquoted into a 96-well microplate, and treated with PMA at 250 ng per 1 ml of the culture medium, to induce lymphocyte proliferation among the splenocytes, and then the EPS of Preparation Example 1 was added thereto dropwise at 0.05 μg, 0.15 μg, 0.5 μg, 1.5 μg or 5 μg per 1 ml of the culture medium. For comparison, a control group was not treated with EPS. The microplate was then cultured for 48 hours in an incubator in which 5% $CO_2$, 37° C. and sufficient humidity were maintained. After the culture, in order to examine the proliferation capability of the cultured cells, MTT (3-(4,5-dimethylthiazol-2-yl)-2,5-diphenyltetrazolium bromide; Sigma, USA) assay was performed for each well of the microplate.

Specifically, cultured cells were treated with MTT solution to obtain a final concentration of 0.1 mg/ml, and then cultured for 4 hours while blocking light with aluminum foils, to induce formazan crystal formation. The supernatant was removed and each well was treated with 150 μl of dimethyl sulfoxide (DMSO), and allowed to stand for 10 minutes, and the absorbance was measured at 540 nm using an ELISA reader. The lymphocyte proliferation capability among splenocytes was calculated by the following equation.

Cell viability (%)=(absorbance of test group/absorbance of control group)×100

The MTT assay was repeated three times and the results are shown in Table 3 below.

TABLE 3

| Treatment concentration | Absorbance (540 nm) | | | Absorbance average and standard deviation | Viability (%) |
|---|---|---|---|---|---|
| Negative control group (no treatment) | 0 | 0.1842 | 0.1526 | 0.1390 | 0.159 ± 0.0008 | 100 |
| PMA | 250 ng/ml | 0.7287 | 0.6074 | 0.6034 | 0.647 ± 0.071 | 406.9 |
| EPS of Preparation Example 1 (μg/ml) | 0.05 | 0.7075 | 0.5181 | 0.6831 | 0.636 ± 0.103 | 400.0 |
| | 0.15 | 0.5581 | 0.6609 | 0.5147 | 0.578 ± 0.075 | 363.5 |
| | 0.5 | 0.4818 | 0.5196 | 0.5127 | 0.505 ± 0.020 | 317.6 |
| | 1.5 | 0.3680 | 0.4890 | 0.4321 | 0.430 ± 0.061 | 270.4 |
| | 5 | 0.3013 | 0.4054 | 0.4779 | 0.395 ± 0.089 | 248.4 |

As shown in Table 3, the EPS of the present invention inhibited the lymphocyte proliferation increased by the treatment of PMA, a non-specific stimulant, among splenocytes, concentration-dependently and significantly. This is an effect of inhibition of excessive immunity due to excessive lymphocyte increase, and this result shows that the EPS can be effectively used for prevention and treatment of autoimmune disorders.

Example 3. Measurement of Splenocyte Proliferation Capability

The splenocyte proliferation capability by EPS treatment was measured in splenocytes by the same method as in Example 2 except that treatment with PMA, a non-specific stimulant, was not conducted, and the results are shown in FIG. 1 and Table 4.

splenocyte concentration-dependently and significantly. The proliferation of splenocytes as described above is an effect of activating the immune system, and this result shows that the EPS can be effectively used for the prevention and treatment of an immune disorder.

Example 4. Measurement of TNF-α Expression 4-1: Preparation of EPS-Treated Cells In order to evaluate the effect of immune enhancement of the EPS of Preparation Example 1, peritoneal macrophages derived from mice were treated with EPS of various concentrations, and TNF-α mRNA and protein expressions were measured.

Specifically, Balb/C mice, about 8 weeks old and weighing about 25 g, were purchased from Hyochang Science, Korea and used in the experiments. 1 ml of 4% thioglycollate was injected to the mice, and after the mice were sacrificed by cervical dislocation, peritoneum was exposed and 10 ml of cold RPMI 1640 was injected into the abdominal cavity, and then, the abdominal cavity was lightly massaged. Thereafter, the cleansing solution was drawn from the abdominal cavity using a 10 ml syringe, and centrifuged at 4° C. for 10 minutes at 1,000 rpm. After removing the supernatant, 1 ml of fresh RPMI 1640 medium was added to the precipitate, and the mixture was aliquoted into a 96-well plate at $3 \times 10^6$ cells/well and then cultured for 3 hours. After the culture, cells which were not adsorbed to the plate were removed and only the adsorbed cells were further cultured for 3 days to obtain mouse peritoneal macrophages.

Then, the cultured macrophages were added to a 96-well plate at 100 μl/well and cultured in an incubator at 37° C. and 5% $CO_2$ for 24 hours. After the medium was discarded, the surface of the cultured cells was washed with a 1×PBS

TABLE 4

| Treatment concentration | Absorbance (540 nm) | | | Absorbance average and standard deviation | Viability (%) |
|---|---|---|---|---|---|
| Negative control (no treatment) | 0 | 0.1842 | 0.1526 | 0.1390 | 0.159 ± 0.0008 | 100 |
| EPS of Preparation Example 1 (μg/ml) | 0.05 | 0.1726 | 0.2 | 0.2352 | 0.203 ± 0.010 | 127.7 |
| | 0.15 | 0.2016 | 0.2357 | 0.2238 | 0.220 ± 0.006 | 138.4 |
| | 0.5 | 0.2312 | 0.2665 | 0.2498 | 0.249 ± 0.006 | 156.6 |
| | 1.5 | 0.3128 | 0.2539 | 0.3182 | 0.295 ± 0.012 | 185.5 |
| | 5 | 0.2914 | 0.295 | 0.2598 | 0.282 ± 0.006 | 177.4 |

As shown in FIG. 1 and Table 4, the EPS of the present invention increased splenocyte proliferation capability in solution (Sigma, USA), and then each well was treated with the EPS of Preparation Example 1 at 0.5 μg/ml, 1.5 μg/ml or 5 µg/ml, and then the cells were cultured for 6 hours, to obtain EPS-treated cells. For comparison, the control group was not treated with EPS.

4-2: Analysis of TNF-α mRNA Expression

RNA was isolated from the EPS-treated cells of Example 4-1 and subjected to polymerase chain reaction (PCR), to analyze TNF-α mRNA expression.

Specifically, total RNA isolation was performed according to the method of the easy-BLUE™ total RNA extraction kit. Then, for cDNA synthesis, 1 µg of total RNA, oligodT 18 and DEPC-DW (Bioneer) were added to RT-PreMix (Bioneer), and reacted at 42° C. for 60 minutes and 94° C. for 5 minutes, to synthesize cDNA. Next, 5 µl of the RT mixed solution containing the cDNA was added to the PCR PreMix (Bioneer), and a forward primer and a reverse primer for TNF-α were added thereto, and PCR was carried out. As for the PCR condition, mRNA was amplified by repeating a set of reactions (at 95° C. for 30 seconds, 55° C. for 30 seconds, and 72° C. for 1 minute) for a total of 30 cycles. Differences in the expression of TNF-α mRNA were examined by electrophoresis on 1.5% agarose gel, and the results are shown in FIG. 2.

In order to perform the RT-PCR, a forward primer (5'-TTCTGTCTACTGAACTTCGGGGTGATCGGTCC-3', SEQ ID NO: 1) and a reverse primer (5'-GTATGAGATAG-CAAATCGGCTGACGGTGTGGCTGACGGTGTGGGG-3', SEQ ID NO: 2) for TNF-α, and a forward primer (5'-AGATCCACAACGGATACATT-3', SEQ ID NO: 3) and a reverse primer (5'-TCCCTCAAGATTGTCAGCAA-3', SEQ ID NO: 4) for GAPDH were used (Bioneer, Korea).

As shown in FIG. 2, the expression of TNF-α mRNA was increased in EPS-treated macrophages of the present invention in EPS treatment concentration-dependent manner as compared to the macrophages not treated with EPS. This indicates an increase in the expression of TNF-α, which inhibits the proliferation and replication of viruses, by macrophage activation, and is the result of verifying the immune enhancement activity of EPS of the present invention.

4-3: Analysis of TNF-α Protein Expression

The EPS-treated cells of Example 4-1 were treated with Protein Extraction Solution (Intron Biotechnology) to dissolve them. The solution was centrifuged at 13,000 rpm for 15 minutes at 4° C., and the protein in the upper layer was recovered, and the concentration of the protein was measured at 595 nm using a Bradford reagent, and the protein amounts of all samples were quantified to 30 µg. The total volumes were made equal using NuPAGE LDS sample buffer (Novex, USA), and the samples were heated at 100° C. for 5 minutes and allowed to stand on ice for 15 minutes. Using the samples, electrophoresis was performed on 10% SDS-polyacrylamide (SDS-PAGE) gel. The bands on the SDS-PAGE gel were transferred to a nitrocellulose membrane under the condition of 4° C. and 300 mM for 1 hour and 30 minutes. The membrane was reacted with Tris-Buffer saline (TBS) containing 0.1% Tween 20 (Sigma, USA) and 5% skim milk for 1 hour to block non-specific binding of antibodies, and washed with TBS-T (Tris-Buffered Saline Tween 20) 3 times at 15 minute intervals.

For the primary antibody reaction, a solution of TNF-α (a product of Abcam) diluted 1,000 times by TBS-T containing 5% skim milk was added to the membrane, which was reacted at 4° C. for 1 hour, and then washed with TBS-T five times for 15 minutes each. For the secondary antibody reaction, a solution of an anti-rabbit polyclonal antibody (Cell Signaling, Danvers, Mass., USA) labeled with horseradish peroxidase (HRP) diluted 5,000 times with TBS-T containing 5% skim milk was added to the membrane, which was incubated at room temperature for 1 hour, and then evenly treated with a chemiluminescent HRP (chemiluminescent HRP) substrate to examine the protein expression pattern. The results are shown in FIG. 3.

As shown in FIG. 3, the expression of TNF-α protein was increased in EPS-treated macrophages of the present invention in an EPS treatment concentration-dependent manner as compared to the macrophages not treated with EPS. This indicates an increase in the expression of TNF-α, which inhibits the proliferation and replication of viruses, by macrophage activation, and is the result of examining the immune enhancement activity of the EPS of the present invention.

The invention claimed is:

1. A method of enhancing immunity or inhibiting excessive immunity in a subject in need thereof, comprising administering a composition comprising
  (a) an extracellular polysaccharide produced by *Ceriporia lacerata*;
  (b) a mycelial culture medium of *Ceriporia lacerata*, said mycelial culture medium containing the extracellular polysaccharide;
  (c) dried powders of the mycelial culture medium containing the extracellular polysaccharide; or
  (d) an extract of the dried powders (c) containing the extracellular polysaccharide,
  as an effective ingredient, to the subject
  wherein the subject suffers from an immune disorder, said immune disorder being at least one selected from the group consisting of dermatitis, allergies, rhinitis, gout, ankylosing spondylitis, rheumatic fever, lupus, fibromyalgia, peritendinitis, scleroderma, silicosis, vitiligo, and conjunctivitis, and
  wherein the enhancing immunity or inhibiting excessive immunity is an increase in splenocyte proliferation and/or an increase in TNF-alpha production in the subject.

2. The method of claim 1, wherein the extracellular polysaccharide comprises 40 to 60 wt % of sugar and 30 to 40 wt % of protein, and has a molecular weight of 100 to 150 kDa.

3. The method of claim 1, wherein the extracellular polysaccharide comprises 43 to 47 wt % of sugar and 33 to 36 wt % of protein, and has a molecular weight of 115 to 125 kDa.

4. The method of claim 3, wherein the sugar contains mannose, galactose and glucose.

5. The method of claim 1, wherein the extracellular polysaccharide is prepared by a preparation method comprising the steps of:
  (a) culturing the mycelia of *Ceriporia lacerata* in a liquid to prepare a mycelial culture medium of *Ceriporia lacerata*,
  (b) drying the mycelial culture medium of *Ceriporia lacerata* to form powders, and
  (c) extracting the powders of the mycelial culture medium of *Ceriporia lacerata* with a solvent, and filtering and concentrating the resultant extract under reduced pressure.

6. The method of claim 5, wherein the liquid of step (a) comprises a culture medium including sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and wherein a pH of the culture medium is 4.5 to 6.0.

7. The method of claim 5, wherein the culturing (a) is conducted under a blue LED light source with a carbon dioxide concentration maintained at 1,000 to 2,000 ppm.

8. The method of claim 1, wherein the extracellular polysaccharide is comprised in an amount of 0.1 to 80 wt % based on the total weight of the composition.

9. The method of claim 1, wherein the subject further suffers from a disorder selected from the group consisting of rheumatoid arthritis, systemic scleroderma, atopic dermatitis, psoriasis, asthma, Guilian-Barre syndrome, dermatomyositis, polymyositis, multiple sclerosis, autoimmune encephalomyelitis, polyarteritis nodosa, temporal arteritis, alopecia areata, pemphigus, aphthous stomatitis, Crohn's disease and Behcet's disease.

10. The method of claim 1, wherein the composition is a pharmaceutical composition and further comprises a pharmaceutically acceptable carrier.

11. The method of claim 1, wherein the composition is a food or a dietary supplement, and further comprises a sitologically acceptable food supplementary additive.

12. The method of claim 11, wherein the food or the dietary supplement is in a form of powders, granules, a tablet, a capsule or a beverage.

13. The method of claim 11, wherein the food or the dietary supplement is a candy, a chocolate, a beverage, a gum, a tea, or a vitamin complex formulation.

14. The method of claim 1, wherein the immune response is an excessive immunity mediated by excessive lymphocyte proliferation.

15. The method of claim 14, wherein the excessive lymphocyte proliferation is caused by a treatment using phorbol 12-myristate 13-acetate.

* * * * *